(12) United States Patent
Auf Der Maur et al.

(10) Patent No.: US 7,258,986 B2
(45) Date of Patent: Aug. 21, 2007

(54) INTRABODIES WITH DEFINED FRAMEWORK THAT IS STABLE IN A REDUCING ENVIRONMENT AND APPLICATIONS THEREOF

(75) Inventors: Adrian Auf Der Maur, Zurich (CH); Alcide Barberis, Zurich (CH); Dominik Escher, Zurich (CH)

(73) Assignee: ESBATech AG, Schlieren (CH)

( * ) Notice: Subject to any disclaimer, the term of this patent is extended or adjusted under 35 U.S.C. 154(b) by 0 days.

(21) Appl. No.: 10/169,179

(22) PCT Filed: Dec. 18, 2000

(86) PCT No.: PCT/IB00/01892

§ 371 (c)(1),
(2), (4) Date: Sep. 24, 2002

(87) PCT Pub. No.: WO01/48017

PCT Pub. Date: Jul. 5, 2001

(65) Prior Publication Data

US 2003/0096306 A1 May 22, 2003

(30) Foreign Application Priority Data

Dec. 28, 1999 (WO) .................. PCT/IB99/02054
Mar. 1, 2000 (WO) .................. PCT/IB00/00218

(51) Int. Cl.
*G01N 33/53* (2006.01)
*C40B 20/00* (2006.01)
*C12P 21/02* (2006.01)

(52) U.S. Cl. .............. 435/7.1; 435/6; 435/DIG. 7; 435/DIG. 5; 435/DIG. 2; 530/388.1; 530/387.1; 530/350

(58) Field of Classification Search .......... 435/7.1, 435/6, 5, DIG. 7, DIG. 5, DIG. 2; 530/387.3, 530/387.1, 388.1, 350
See application file for complete search history.

(56) References Cited

U.S. PATENT DOCUMENTS 6,153,380 A * 11/2000 Nolan et al. ............... 435/6
2003/0017149 A1 1/2003 Hoeffler et al.

FOREIGN PATENT DOCUMENTS

WO WO99/28502 6/1999

OTHER PUBLICATIONS

Martineau et al, J. Mol. Biol. (1999), 292, 921-929.*
Cattaneo et al., "The Selection of Intracellular Antibodies," *TIBTECH*, 17:115-121 (1999).
Davies, et al., Single Antibody Domains as Small Recognition Units: Design and In Vitro Antigen Selection of Camelized, Human VH Domains with Improved Protein Stability, *Protein Engineering*, 9:531-537 (1996).
DeHaard, et al., "Selection of Recombinant, Library-Derived Antibody Fragments against p24 for Human Immunodeficiency Virus Type 1 Diagnostics,", *Clinical and Diagnostic Laboratory Immunology*, 5:636-644 (1998).
Hanes et al., "Ribosome Display Efficiently Selects and Evolves High-Affinity Antibodies in vitro from Immune Libraries," *Proc. Natl. Acad. Sci. USA*, 95:14130-14135 (1998).
Martineau et al., "Expression of an Antibody Fragment at High Levels in the Bacterial Cytoplasm," *J. Mol. Biol.*, 280:117-127 (1998).
Martineau et al., "In vitro Folding and Thermodynamic Stability of an Antibody Fragment Selected in vivo for High Expression Levels in *Escherichia coli* Cytoplasm," *J. Mol. Biol.*, 292:921-929 (1999).
Portner-Taliana et al., "In vivo Selection of Single-Chain Antibodies Using a Yeast Two-Hybrid System," *Journal of Immunological Methods*, 238:161-172 (2000).
Proba et al., "Antibody scFv Fragments Without Dislfide Bonds Made by Molecular Evolution," *J. Mol. Biol.*, 275:245-253 (1998).
Reiter et al., "An Antibody Single-domain Phage Display Library of a Native Heavy Chain Variable Region: Isolation of Functional Single Domain VH Molecules with a Unique Interface," *J. Mol. Biol.*, 290:685-698 (1999).
Visitin et al., "Selection of Antibodies for Intracellular Function Using a Two-Hybrid in vivo System," *Proc. Natl. Acad. Sci. USA*, 96:11723-11728 (1999).
Worn et al., "Correlation between in vitro Stability and in vivo Performance of Anti-GCN4 Intrabodies as Cytoplasmic Inhibitors," *J. Biol. Chem.*, 275:2795-2803 (2000).

* cited by examiner

*Primary Examiner*—T. D. Wessendorf
(74) *Attorney, Agent, or Firm*—Marshall, Gerstein & Borun LLP

(57) ABSTRACT

A method for the isolation of CDRs in a defined framework that is stable and soluble in reducing environment is described as well as thus obtainable scFv. Starting from such scFv with defined framework a scFv library can be generated wherein the framework is conserved while at least one complementary determining region (CDR) is randomized. Such library, e.g. in yeast cells, is suitable for screening for antibody/CDR-interactions or for screening for antibodies.

6 Claims, 9 Drawing Sheets

INTRABODIES WITH DEFINED FRAMEWORK THAT IS STABLE IN A REDUCING ENVIRONMENT AND APPLICATIONS THEREOF

CROSS REFERENCES TO RELATED APPLICATIONS

This application claims the priority of PCT patent application IB99/02054, filed Dec. 28, 1999 and the priority of PCT patent application IB00/00218, filed Mar. 1, 2000 the disclosure of which are incorporated herein by reference in its entirety.

TECHNICAL FIELD

The present invention concerns single chain fusions of variable regions of heavy and light chains of an antibody (scFv), in particular such scFv expressed within a cell (intrabodies) with a defined, stable, framework.

BACKGROUND ART

Antibodies are preferred tools for biochemical and molecular biology research, diagnostics and medical applications due to their high affinity and specificity to the antigen and due to their relatively high stability in vitro and in vivo. Antibodies are made of two heavy and two light chains, which contain the variable regions at their N-termini and which are linked by disulfide bridges. Single chain antibodies have been engineered by linking fragments of the variable heavy and light chain regions (scFv). Each variable domain contains three complementary determining regions (CDR) embedded in a framework. These CDRs are responsible for the interaction with the antigen. Each variable heavy and light region contains an intradomain disulfide bridge, which was reported to be critical for stability of the single chain antibody (Biocca et al., 1995; Derman et al., 1993).

The most commonly used technique to identify single chain antibodies which bind specific epitopes is by phage display and variations thereof (for review see Hoogenboom et al., 1998). This screening system has major advantages over conventional techniques like immunization or hybridoma technique, namely that it can uncover monoclonal single chain antibodies within a relatively short time.

Single chain antibodies expressed within the cell (e.g. cytoplasm or nucleus) are called intrabodies. Due to the reducing environment within the cell, disulfide bridges, believed to be critical for antibody stability, are not formed. Thus, it was initially believed that applications of intrabodies are not suitable. But several cases are described showing the feasibility of intrabodies (Beerli et al., 1994; Biocca et al., 1994; Duan et al., 1994; Gargano and Cattaneo, 1997; Greenman et al., 1996; Martineau et al., 1998; Mhashilkar et al., 1995; Tavladoraki et al., 1993). In these cases, intrabodies work by e.g. blocking the cytoplasmic antigen and therefore inhibiting its biological activity.

Up to now, intrabodies were most of the time derived from monoclonal antibodies which were first selected with classical techniques (e.g. phage display) and subsequently tested for their biological activity as intrabodies within the cell (Visintin et al., 1999). Although successful intrabodies are described (see above), it is today completely unpredictable whether such an intrabody is functional within the cell (for reviews see Cattaneo, 1998; Cattaneo and Biocca, 1999). The reasons are most probably the different environments: Phage display and other classical techniques are performed under oxidizing conditions, therefore disulfide bridges are formed, whereas intrabodies must function in reducing conditions. This reducing environment can lead to insufficient solubility of the intrabody and hence they form non-functional aggregates. The solubility of an intrabody can be modified by either changes in the framework (Knappik and Pluckthun, 1995) or the CDRs (Kipriyanov et al., 1997; Ulrich et al., 1995).

However, the hitherto known systems are limited with regard to their application to detect intracellular targets. Therefore, it is a growing need to have a reliable technology and system to screen directly for intrabodies specific for an antigen.

In WO 99/36569, Wittrup et al. describe a method to display proteins and scFv on the cell wall of yeast by using a yeast endogenous protein fragment derived from Aga2p for localization on the cell wall. Libraries of proteins and scFv can be screened interacting with other proteins. Other related systems are described in EP 0 407 259 (Boquet et al., 1991). These systems are comparable to the phage display screening where the protein or peptide library is also presented on the surface. However, these techniques cannot be used for intracellular screenings to identify intrabodies.

The patent document JP 11000174 (Kyoko et al., 1999) describes the use of yeast Pichia pastoris for high level expression and secretion of antibody Fab fragments. This yeast is famous for its high secretion level and is therefore preferably used for this application. The secreted antibody can be harvested by purification of the supernatant. Furthermore, in EP 0 590 067, WO92/22324, JP 060 30 778, U.S. Pat. Nos. 5,698,435, 5,595,889, JP 10313876 yeast is used for production of secreted proteins or antibodies. EP 0 698 097 and WO 94/25591 disclose application of the production and secretion of only the heavy chain or fragments thereof for further applications. JP 0 902 0798; JP 051 05700; and JP 050 97704 describe methods of yeast secretion to obtain hepatitis vaccine when administered to the human body or to organisms in general.

It is also already known from WO 99/28502 to use yeast for screenings of single chain antibodies. Said application discloses the use of a DNA construct library for a single chain monoclonal antibody fusion reagent. his scFv library (therein termed sFv library) is subsequently used for screenings. However, it has now been found that the stability and solubility of intrabodies can vary dramatically due to the use of a non specified framework. Furthermore, it could be shown that a direct correlation exists between the in vivo performance and the in vitro stability and solubility. Therefore, the use of mRNA derived libraries of different scFv fragments is limited in view of the possibility to identify CDR which have a high affinity to the antigen because, although the CDRs would in principle show the required high affinity to the antigen, the corresponding framework is not soluble enough and thus aggregates, making it impossible to select for this monoclonal scFv. Thus, there is still a need for improved antibodies, or intrabodies, respectively.

The growing applications of scFv directed against intracellular targets raise the need for reliable screening systems for intrabodies. Cytoplasmic targets of scFv are the most demanding application due to the instability of the scFv under reducing conditions and the unpredictability of the antibody stability. This stability and also solubility problem can be solved by using defined frameworks, optimized for intracellular application.

DISCLOSURE OF THE INVENTION

Hence, it is a general object of the present invention to provide methods for the isolation of a scFv or intrabody with defined framework that is stable and soluble in reducing environment.

A further object of the present invention is such a scFv or intrabody with defined framework that is stable and soluble in reducing environment.

Another object of the present invention is a scFv or intrabody with defined framework that is stable and soluble in reducing environment that is modified to provide unique restriction sites in the CDR/framework-connecting regions.

Another object of the present invention is a library of scFvs or intrabodies with defined framework that is stable and soluble in reducing environment, and randomly or definedly variated CDRs.

Another object of the present invention is a method for screening for antigen binding CDRs using such scFvs or intrabodies with defined framework that is stable and soluble in reducing environment, and varied CDRs, or a library of such scFvs or intrabodies.

Another object of the present invention is a method for screening for further antigens using such scFv or intrabodies or library, respectively.

Another object of the present invention is a method for the identification of intrabodies with frameworks that are soluble and stable under reducing conditions.

The intrabodies of the present invention can furthermore be used as agent in therapy, diagnosis or prevention of diseases and several applications in plants, such as functional knock out of a specific protein activity. The intrabodies can be used as such or as DNA encoding such scFv.

In the scope of the present text, the terms scFv and intrabody are largely used as synonyms, however, it has to be understood that, while the stability and solubility of the intrabodies (scFv) with defined framework of the present invention in reducing environment, e.g. within a cell, is necessary for the present invention, the application of such intrabodies (scFv) etc. is not restricted to applications within a cell.

By only introducing amino acid changes within the CDRs, such a framework according to the present invention greatly increases the possibility to identify monoclonal antibodies showing the desired biological function of specific antigen recognition. Such changes in the CDRs of the scFv can be performed as random changes without changing the defined framework, suitable for the cytoplasmic application of intrabodies.

In order to perform screenings of monoclonal single chain antibodies within the cell, one has to use a framework which is adapted to the redox environment of the cytoplasm. Therefore a framework has to be stable and soluble enough even in the absence of disulfide bridge. Most of the scFv, however, are known not to fold into the proper structure under reducing conditions or in the absence of the cysteine, responsible for the formation of intradomain disulfide bridges. Thus, in the scope of the present invention several frameworks containing identical CDRs have been compared and dramatic differences in the in vivo performance have been observed. By the inventive method the best performing framework containing the defined CDRs for antigen recognition can be selected. This method is performed by using an intrabody to a known antigen as starting material. The linker used to connect the variable regions of heavy and light chain is not critical. It must, however, provide sufficient solubility and flexibility to ensure suitable contact and folding for an interaction between CDRs and antigen. Suitable linkers have a typical length of about 5-60 amino acids, usual regular series of glycine and in order to enhance solubility 1 to 3 serine.

Such an inventive method for the isolation of an scFv with defined framework that is stable and soluble in a reducing environment is defined by the following steps:

a) a scFv library with varied frameworks and constant CDRs is generated by mutation of at least one framework encoding region of DNA sequence of a scFv to a known antigen and by introduction of such mutations into suitable expression vectors, b) host cells able to express a specific known antigen and only surviving in the presence of antigen-scFv-interaction are transformed with said scFv library, c) the thus transformed host cells are cultivated under conditions suitable to express the antigen and the scFv and allowing cell survival only in the presence of antigen-scFv-interaction, d) the scFv expressed in surviving cells and having a defined framework that is stable and soluble in reducing environment is isolated.

In a preferred embodiment the host cell is an eukaryotic cell, in particular a yeast cell.

By the above described method a scFv with defined framework is obtainable. Such framework is also an object of the present invention. Such a framework can be modified to comprise specific restriction sites allowing the selective exchanging of at least one CDR. Preferably said restriction sites are located within the framework flanking a CDR.

The invention furthermore provides a method for the generation of a scFv encoding DNA with a framework suitable for selective alterations in the CDR region, wherein specific restriction sites are introduced into the sequence of a defined, stable and soluble scFv encoding DNA by means of site directed mutagenesis whereby said restriction sites are preferably located within the framework and whereby the substitution of the nucleotides to generate the restriction site does not affect the amino acid sequence.

An improved scFv with defined framework that is stable and soluble in a reducing environment can also be obtained by a method that is also an object of the present invention, wherein at least two variations of at least two different frameworks that are stable and soluble in a reducing environment, preferably frameworks of the present invention are combined to produce a scFv with defined framework.

A scFv obtainable by the above described method is also an object of the present invention. In such framework it is preferred that at least one of the variations is preceding the CDR1 of the variable light chain and/or at least one of the variations is located between CDR2 and CDR3 of the variable heavy chain.

In a much preferred embodiment the scFv of the present invention comprises at least 2 variations preceding CDR1 of the variable light chain and at least 2, preferably at least 4 variations located between CDR2 and CDR3 of the variable heavy chain, in particular a scFv comprising the framework defined in SEQ ID NO 1.

In order to specifically randomize the CDRs in such framework, silent changes, still coding for the same amino acid sequences but using different codons, can be introduced which lead to the generation of unique restriction sites (see also above). While the restriction sites can be located anywhere in the CDR/framework-connecting regions, it is preferred if they are located in the framework flanking each individual CDR. By this, each individual CDR can be replaced by introducing random or defined sequences. This allows to select for novel CDR in the intrabody showing a high affinity to the antigen.

When additional sequences, like localization signals or activation domains are introduced into a non-defined framework, stemming from a scFv library, it is possible that due to this modifications, the biological activity—even if hitherto present—is lost, e.g. the scFv gets insoluble. Therefore it is of advantage to use a defined framework of the present invention to a known antigen and subsequently introduce such modifications at different locations in the intrabody (N- and C-terminal or within the coding sequence of the scFv) and select for the maintenance of the original function. WO 99/28502 describes several possibilities to introduce a localization signal. The activation domain used for interaction screenings to an antigen has been described in WO 99/98502 to be introduced at the C-terminus of the scFv library. It has now been found that by the method of the present invention also frameworks can be selected which accept additional sequences at different locations, e.g. the activation domain at the N-terminus, which still perform similar to their scFv counterparts, having no activation domain, in the antagonistic function. Therefore, e.g. in the framework further described in the following examples, introducing the activation domain N-terminal does not impair the antibody function.

Starting from an intrabody of the present invention with a defined framework that is stable and soluble in reducing environment, scFv or intrabodies, respectively, containing CDR libraries can be generated.

A suitable method for the generation of a CDR library with a defined framework, that is stable and soluble in a reducing environment is a method of the present invention, wherein DNA sequences encoding a scFv of the present invention are digested to replace at least one CDR per sequence by a modified CDR. Preferably the modified CDR is generated by random changes. By such method a library of intrabodies with at least one randomized CDR and defined framework that is stable and soluble under reductive conditions can be generated.

The intrabodies of the present invention containing CDR libraries can be used to screen and select for clones having a high affinity to the antigen. Such a method for screening for CDRs interacting with a specific antigen is also an object of the present invention and comprises host cells transformed with a nucleic acid sequence, in particular a DNA sequence, encoding a known antigen which are further transformed with a randomized CDR library with defined framework that is stable and soluble in a reducing environment, whereby the antigen and/or the scFv are linked to a marker system or part of a marker system thus that the cell cultured under selective conditions only survives in the presence of antigen/scFv-interaction, that thus transformed cells are cultivated under selective conditions, and that surviving cells are cultured and the intrabodies harvested.

In a preferred embodiment of the present invention the framework is a framework of the present invention and the cell is an eukaryotic cell, in particular a yeast cell.

In a much preferred embodiment of the present invention the DNA sequence encoding the antigen and the DNA sequence encoding the scFv both encode chimeric molecules with the antigen or scFv, respectively, both linked to part of a transcription activating system linked to a survival allowing marker, more preferably the antigen is fused to a DNA binding domain and the scFv is fused to a transcriptional activator domain or the antigen is fused to a transcriptional activator domain and the scFv is fused to a DNA binding domain.

The intrabodies of the present invention containing CDR libraries can be used to screen and select for clones having a high affinity to the antigen. This can either be achieved by blocking the intracellularly located antigen in its biological function or by assaying for direct interaction of the CDRs embedded in the defined framework to the antigen. Direct interaction can, preferably, be monitored by a transcriptional readout, preferably by the expression of the HIS3 gene. Adding 3-aminotriazol (3AT) to the medium, allows to select for higher affinity of the CDRs to the antigen under said predetermined conditions. Host cells which are able to express a specific known antigen only survive in the presence of antigen-scFv-interaction under said conditions, preferably in the presence of sufficiently strong antigen-scFv interaction. The term sufficiently strong as used herein is defined as protein-protein interactions having a $K_D$, measured by BIAcore, which is $>1\times10^{-6}$ M, preferably a $K^D>1\times10^{-8}$ M and more preferably a $K_D>1\times10^{-10}$ M. Such a selection step can further be applied to perform affinity maturation by random or selective changes of amino acids in the CDR (preferably CDR1 and CDR2 of the light and heavy chain) and subsequently select out of this pool for growth on increased 3AT concentration.

As already mentioned above, hitherto known and used scFv libraries stem from the isolation of mRNA from preferably spleen which is known to have a high accumulation of B cells and therefore rearranged antibodies are expressed. Such a library has the drawback that it has been pre-selected (positive and negative selection) not to react against epitopes present in this organism. This guarantees that only antibodies can mature and be activated which do not start an autoimmune reaction. However, due to this selection steps, not all possible amino acid combinations are present in such a "natural" scFv library. For several in vitro and diagnostic applications, antibodies are required interacting with proteins which are conserved among species. For such proteins or peptides, it might be very difficult to find strong interacting monoclonal antibodies in "natural" scFv libraries due to the pre-selection steps. Furthermore, the frameworks present in such "natural" libraries are not optimized, therefore insufficient or variable solubility and/or stability, respectively, generates problems. Therefore it is of great advantage to use only CDR random libraries comprising a framework of and/or obtainable with the method of the present invention and, covering some or, preferably, all possible combinations of amino acid sequence in these regions.

In order to further describe the present invention, a stable and soluble intrabody framework with defined complementary determining regions (CDRs) directed against a yeast intracellular transcription factor Gcn4p was selected. This defined framework was used to replace the CDRs by random sequences. These CDR libraries are screened to identify new CDRs which provoke a demanded biological activity (in vivo effect of the CDRs):

a) Molecular interactions which occur naturally within the cell (e.g. in human cells or any other heterologous cells) are reconstituted in a suitable cell, preferably yeast, or yeast endogenous interactions are used. A subsequent screening identifies high affinity CDRs due to the interference of these CDRs with the biological activity of the reconstituted or endogenous molecules. Such an antagonistic CDR could e.g. function by blocking two proteins involved in signal transduction pathways.

b) Agonistic CDRs are selected which induce a demanded biological activity on the reconstituted or endogenous molecules.

The random CDRs embedded in the stable framework can further be used to identify interactions of the CDR with an antigen based on interaction screenings:

a) It could be shown that the selected framework can be fused to a transcriptional activation domain and still retains its function. This chimeric intrabody is used to select for high affinity CDRs against a given antigen fused to a DNA-binding domain or a transcription factor which possesses DNA-binding activity. Upon interaction of the antigen and the CDRs, the transcriptional activation domain mediates gene expression of a selectable marker gene thus allowing survival of this cell under selective conditions.

b) A reconstituted molecular interaction based on hybrid technique (fusion of one partner to activation domain, the other if necessary to DNA-binding domain) can be blocked by specific, high affinity CDRs.

It was also found that different mutations in the framework but constant CDRs of the intrabody have an effect on its in vivo performance by changing the stability and solubility of the intrabody. The framework contributes the major part to the stability and solubility of an intrabody. Nevertheless, certain mutations in the CDRs might also affect solubility and stability of the intrabody. Therefore it might be advantageous to preselect the random CDRs embedded in a defined framework by a functional quality control (see below).

The present invention furthermore provides a method for the identification of intrabody frameworks or intrabodies wherein suitable host cells are transformed with a library and a marker system, whereby said library is a fusion product of an intrabody library and at least part of said marker system, wherein said marker system is only activated in the presence of a fusion protein encoding a soluble and stable intrabody framework, and culturing said cells under conditions allowing the identification and selection of cells expressing a soluble and stable intrabody framework.

In a preferred embodiment of the present invention said library is a fusion product of an intrabody library and a marker protein. Preferably said marker protein has a selectable activity, in particular an enzymatic activity or fluorescence activity. A marker protein that can be used in such a method is e.g. the GFP protein or any mutant thereof.

In another preferred embodiment of the present invention said library is a fusion product of an intrabody library and a DNA binding protein that can activate transcription of a marker gene whose transcription is under control of said DNA binding protein. A suitable DNA binding protein is e.g. p53.

In a further preferred embodiment of the present invention said method comprises suitable host cells that are transformed with a library that encodes proteins comprising an intrabody and one part of a transactivation system and said cells further express a second protein comprising at least the second part of said transactivation system, whereby said transactivation system is linked to a survival allowing marker and said cells only survive under selective conditions in the presence of an interaction between said two fusion proteins.

In a more preferred embodiment said library encoded proteins comprise a transcriptional activation domain and said second proteins comprise a DNA binding domain or said library encoded proteins comprise a DNA binding domain and said second proteins comprise a transcriptional activation domain.

In a further preferred embodiment said second proteins comprise a DNA binding domain or a transactivation domain, respectively, and a protein interacting with a constant region of said library encoded protein. The term constant region as used herein encompasses any protein domain or any contiguous stretch of amino acids that is encoded by the library construct and can serve as protein interacting partner and said term includes e.g. parts of the intrabody or Gal11p.

An scFv with defined framework obtainable by the above methods is also an object of the present invention, in particular for the use in a method of the present invention.

The same methods can also be applied for the screening of any scFv library to identify soluble and stable frameworks that may e.g. be used as starting material for a scFv or CDR library, in particular libraries of the present invention.

Another object of the present invention is to provide a method for screening for an antigen interacting with an scFv, wherein host cells expressing at least one antigen of interest are transformed with at least one scFv with defined framework that is stable and soluble in reducing environment, or with a randomized CDR library with defined framework that is stable and soluble in reducing environment, whereby the antigens and/or the scFvs are linked to a marker system or part of a marker system thus that the cell cultured under selective conditions only survives in the presence of antigen/scFv-interaction, that thus transformed cells are cultivated under selective conditions, and that surviving cells are cultured and the scFvs harvested.

In a preferred embodiment of the present invention the framework is a framework of the present invention and the cell is an eukaryotic cell, in particular a yeast cell.

In a much preferred embodiment of the present invention the DNA sequence encoding the antigen and the DNA sequence encoding the scFv both encode chimeric molecules with the antigen or scFv, respectively, both linked to part of a transcription activating system linked to a survival allowing marker, more preferably the antigen is fused to a DNA binding domain and the scFv is fused to a transcriptional activator domain or the antigen is fused to a transcriptional activator domain and the scFv is fused to a DNA binding domain.

The invention furthermore provides an scFv with defined framework as therapeutic or diagnostic or prophylactic agent and the use of the scFv with defined framework for intracellular screenings.

For all purposes of the present invention eukaryotic cells are preferred, whereby yeast cells are especially preferred due to their specific features including e.g. fast growth, positive selection, growth selection and efficient transformation and selection thereof.

MODES FOR CARRYING OUT THE INVENTION

Quality Control of the scFv and CDR Libraries

The term "quality control" defines an assay that allows the selection of a stable and soluble intrabody from a scFv library.

For this purpose a fusion of the scFv library to a transcriptional activation domain (in this case Gal4AD) and a constant region (in this case Gal11P aa 263-352) is generated. Stability of the fusion protein depends on the stability and the solubility of the scFv portion. The constant Gal11P domain interacts with the dimerization domain of Gal4 (residues 58-97, part of the Gal 4 DNA-binding domain (DBD) (Barberis et al., 1995)).

Figure 1A:
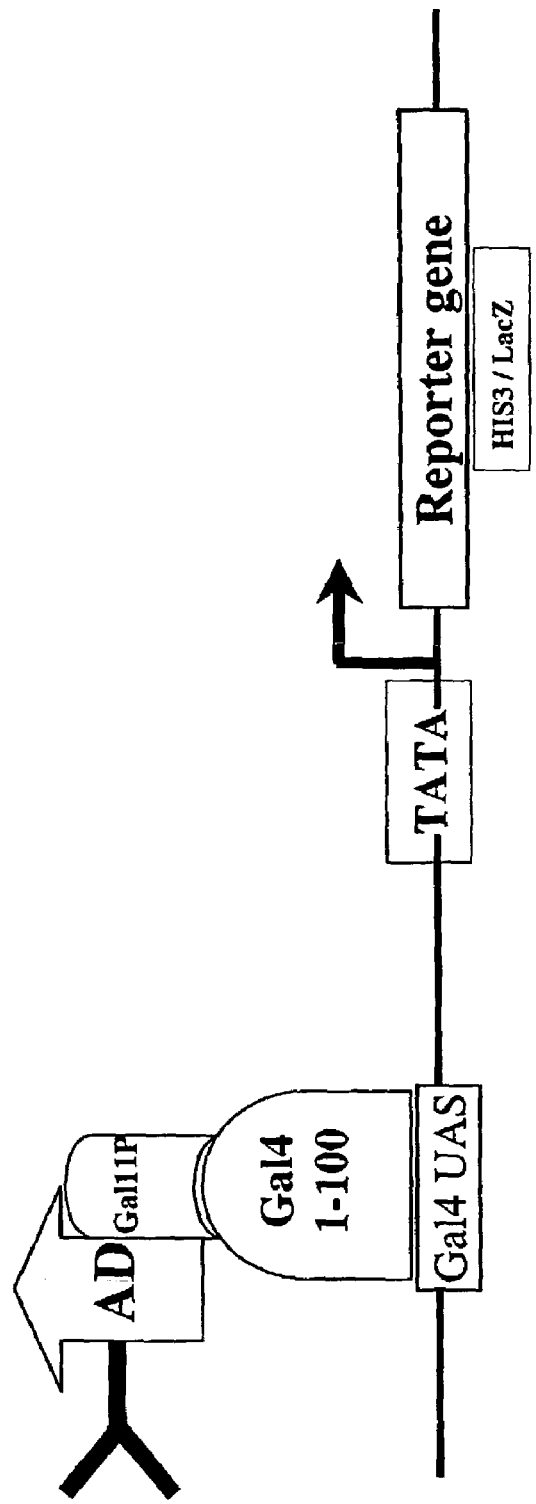
FIG. 1A shows how a quality control of the scFv or CDR library may be performed.

This library is transformed into a yeast cell expressing the Gal4 DBD (residues 1-100) which binds to the promoter of a selectable marker gene (e.g. HIS3/LacZ). Growth of this host cell is only mediated when the tested intrabody shows the demanded solubility and stability and therefore can sufficiently interact via Gal11P with the Gal4 DBD (see FIG. 1A).

Solubility Correlates with Gene Activation

The principle of the quality control system as described in the present invention was demonstrated using a number of well characterised scFvs. These possess essentially identical antigen binding properties but different in vitro stabilities. The different scFv fragments were expressed as Gal11P-Gal4AD fusion proteins. The Gal4 dimerization domain (residues 58-97) was fused tom the C-terminus of LexA and transformed into the reporter strain YDE173, containing reporter genes under the control of 6× LexA binding sites (see below).

As stated above, the intracellular stability and solubility of the Gal11P-Gal4AD-scFv fusion proteins depends on the scFv portion. Therefore, only stable and soluble scFv fusion proteins interacting sufficiently with LexA-Gal4(58-97) are able to activate reporter gene expression (e.g. β-galactosidase)

Figure 1B:
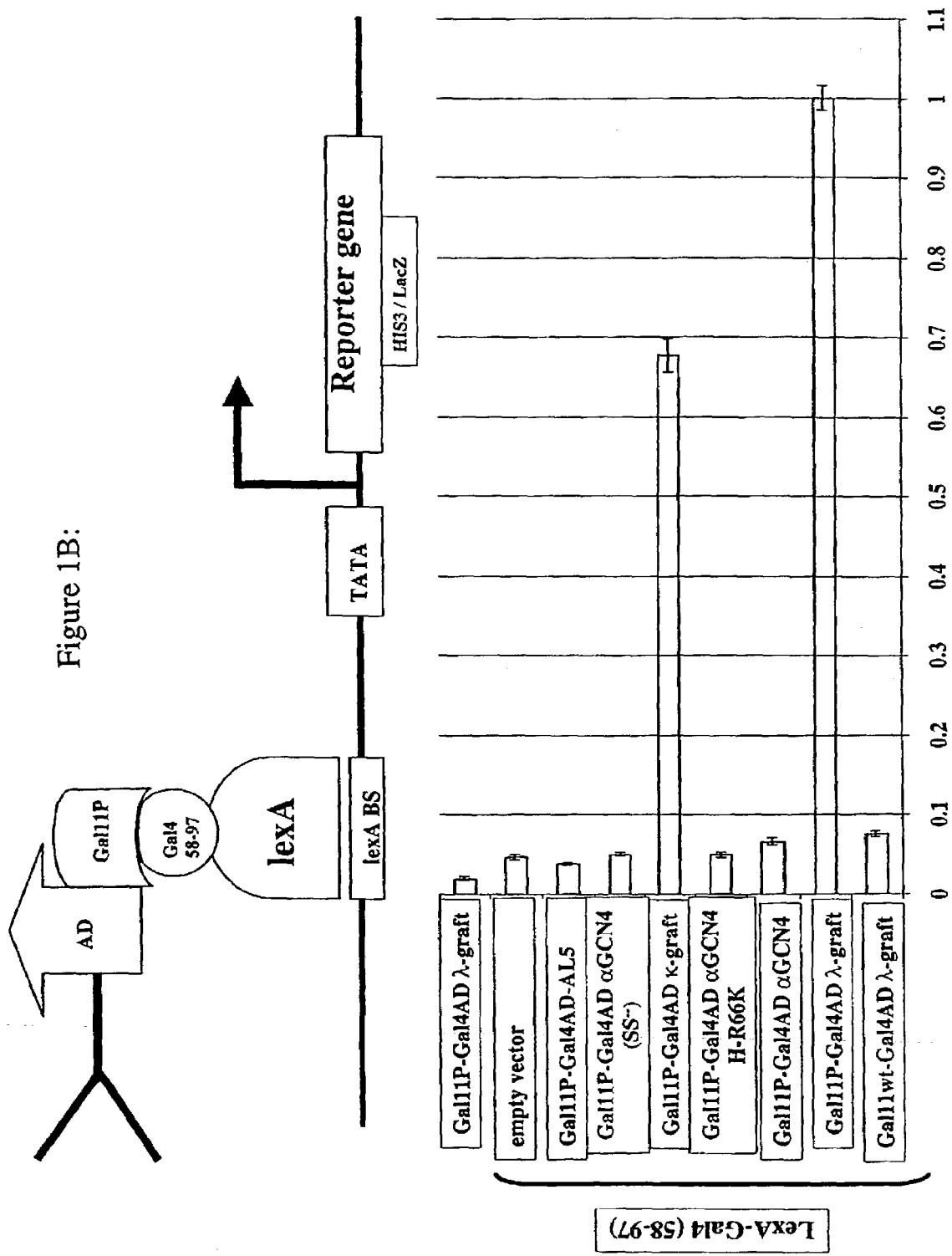
FIG. 1B shows that solubility of the scFv fusion proteins correlates with reporter gene activation.

The wt allele of Gal11 does not interact with the Gal4 dimerization domain (residues 58-97). A fusion of any single chain with the Gal11 wt allele is therefore unable to activate the reporter gene and serves as a negative control. This was demonstrated using a Gal11wt-Gal 4AD-λ graft fusion construct (see FIG. 1B).

Neither the bait (LexA-Gal4(58-97)) nor the scFv fusion protein alone activate reporter gene expression.

Only two out of six tested scFv fragments were soluble and stable enough to activate reporter gene expression in our quality control system. The framework stabilized λ-graft and the κ-graft are the most stable variants. This result correlates perfectly with fractionation analysis, where only the λ- and κ-graft were found in the soluble fraction. (see FIG. 6).

ScFv Fragments Cytoplasmically Expressed in Yeast

Suitable scFv fragments are e.g. the anti-GCN 4 wild-type scFv that has originally been obtained by ribosome display from a library constructed from an immunized mouse (Hanes et al., 1998). The antigen was a double proline mutant of the Gcn4p leucine zipper, called 7P14P (indicating that positions 7 and 14 of the zipper domain are mutated to Pro residues), which forms a random coil in solution (Leder et al., 1995). The scFv fragment prevents dimerization of the wild-type Gcn4p coiled coil peptide in vitro (Berger et al., 1999), as it also binds the wild-type peptide as a monomer in a random coil conformation. The anti-GCN4 scFv fragment referred to as "wild-type" in connection with the present invention has been measured to have a dissociation constant of $4 \cdot 10^{-11}$M from the leuzine zipper peptide (Hanes et al., 1998).

In the scope of the present invention, several different mutants of this scFv were investigated. Besides the anti-GCN4 wild-type, a destabilized variant of the anti-GCN4 wild-type, which carries the H-R66K mutation [termed anti-GCN4(H-R66K)], served as an example for a Gcn4p binding scFv fragment with essentially identical antigen binding properties, but with slightly decreased in vitro stability (see below). The Arg residue at position H-66 (numbering according to Kabat et al., 1991) is far away from the antigen binding pocket and usually forms a double hydrogen bond to Asp H-86. Arg at position H-66 was shown previously to result in higher protein stability than a Lys in the levan binding A48 scFv fragment (Proba et al., 1998; Wörn and Plückthun, 1998a). Moreover, a Val-Ala variant of the anti-GCN4 scFv fragment [termed anti-GCN4 (SS--) was tested, where both intradomain disulfides were replaced by Val-Ala pairs (L-C23V, L-C88A, H-C22V, H-C92A). These mutations had been shown to act slightly stabilizing compared with the reduced dithiol form of the p185HER2 binding 4D5 scFv fragment before, and it had been speculated that they might improve the performance of intrabodies (Worn and Plückthun, 1998b).

Two additional variants were engineered by grafting (Jones et al., 1986) the anti-GCN4 CDR (complementarity determining region) loops to another framework. As the acceptor framework the so-called "hybrid" scFv was chosen (Wörn and Plückthun, 1999). This acceptor framework is composed of the $V_L$ domain of the 4D5 scFv fragment and the $V_H$ domain of the A48++(H2) scFv fragment. It had been rationally designed from a series of stabilized domains and stands out for its extraordinary stability, as demonstrated by denaturant induced equilibrium unfolding, and a high expression yield (Wörn and Plückthun, 1999). Two CDR-grafted variants with the anti-GCN4 scFv CDRs and the "hybrid" scFv framework were prepared by total gene synthesis. As the anti-GCN4 wild-type loop donor carried a light chain, while the acceptor "hybrid" framework carried a κ light chain, the loop grafting was not straight-forward. Therefore, two different variants were designed, one more "κ-like" (termed κ-graft), the other more "λ-like" (termed λ-graft). These two variants differ only in seven residues in the $V_H$-$V_L$ interface region, potentially influencing the orientation of the two domains to each other. The ampicillin-binding scFv fragment AL5 (A. Krebber et al., unpublished) served as a negative control for a scFv fragment not binding Gcn4p.

Anti-GCN4 scFv Intrabodies Inhibit the Transactivation Potential of Gcn4p

The anti-GCN4 scFv was initially tested for its biological activity expressed from several yeast vectors including GAL1 and ADH-driven promoters. In addition, the nuclear localization signal (NLS) from SV40 large T-antigen was fused N-terminally to the anti-GCN4 scFv. Of the combinations tested, the anti-GCN4 scFv showed the strongest biological effect when expressed from the actin-1 promoter without any NLS using the pESBA-Act expression vector (see Examples) with TRP1 selection marker and 2 μ origin (data not shown). This vector was subsequently used for all further experiments.

Figure 3A:
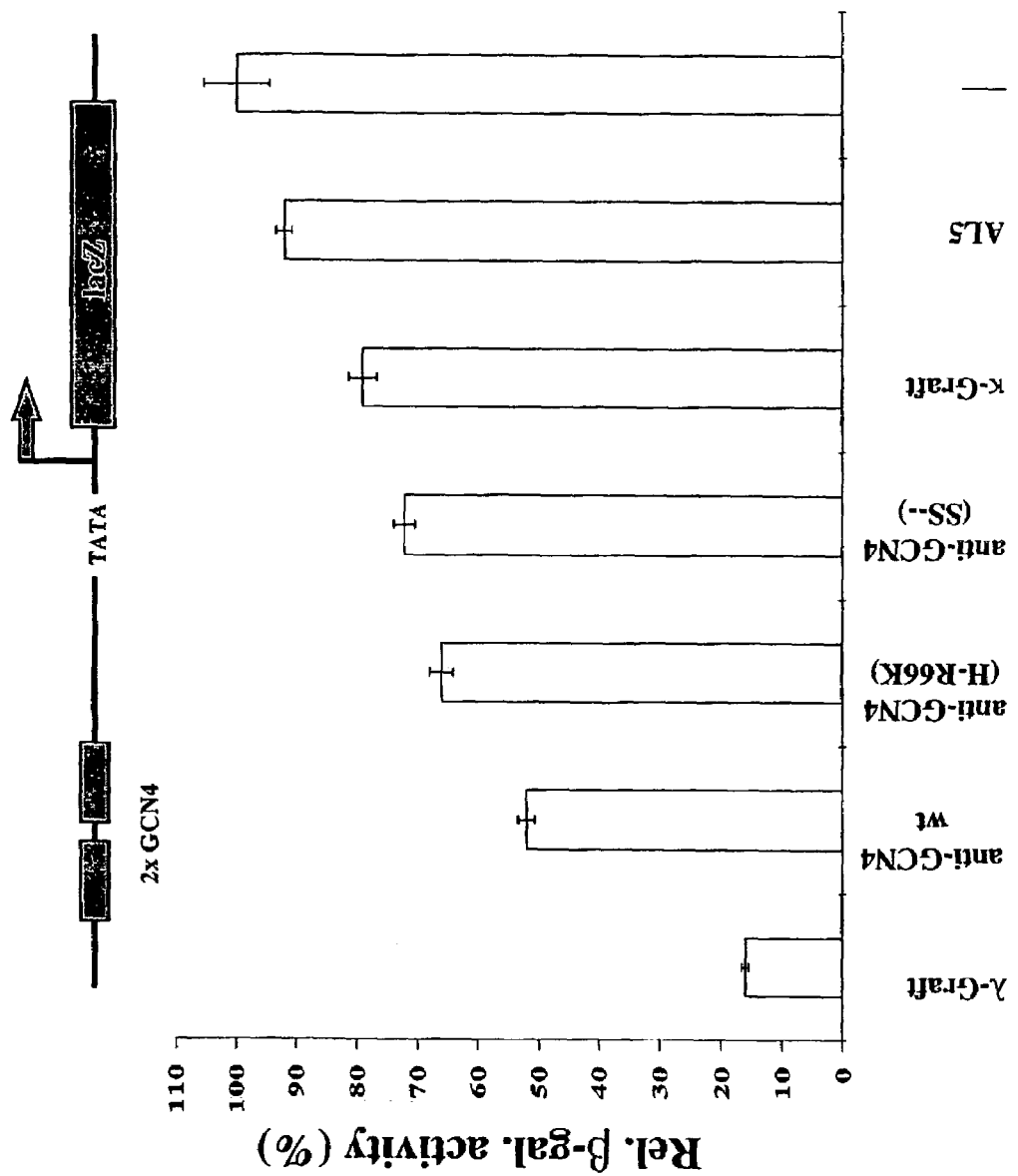
FIG. 3A shows in vivo performance of different scFv fragments on gene expression of a Gcn4p dependent LacZ reporter gene.

The in vivo effect of expressing the different scFv fragments on GCN4 dependent LacZ expression is depicted in FIG. 3A. The reporter construct (YAdM2xGCN4-150) contained two Gcn4p binding sites at position −150 relative to the TATA box and was integrated into the yeast genome. Relative β-galactosidase activity (Rel. β-gal. activity) driven by endogenous Gcn4p was arbitrarily set to 100%. AL5 is an ampicillin binding scFv fragment and serves as negative control. Besides the anti-GCN4 wild-type (wt), a destabilized point mutant [anti-GCN4(H-R66K)], a cysteine-free variant of the anti-GCN4 wild-type (anti-GCN4(SS⁻⁻)], and two framework stabilized variants of anti-GCN4 (κ-graft and λ-graft) were tested. The stabilized λ-graft was the most active intrabody, whilst the destabilized H-R66K point mutant and the cysteine-free variant of anti-GCN4 showed decreased activity, compared to the anti-GCN4 wild-type. The decreased activity of the κ-graft is believed to be due to its low binding affinity (see Table 1). The destabilized point mutant anti-GCN4 (H-R66K) was less efficient in inhibition of GCN4 dependent reporter gene activity, compared to the wild-type scFv. The pattern of Gcn4p transactivation inhibition was highly reproducible and was also confirmed when using a different assay method, where β-galactosidase reporter activity was measured after disrupting the cells by glass beads or freeze-thaw cycles for lysis and normalizing the β-galactosidase activity to protein concentration (Escher and Schaffner, 1997) (data not shown).

TABLE 1

| Protein | $K_D$ [M] | measured β-galactosidase activity (%) | approximate onset of denaturation ([M]) |
|---|---|---|---|
| anti-GCN4 wt | $4.36 \pm 0.09 \cdot 10^{-11}$ | 52 ± 1.38 | 1.7 |
| anti-GCN4 (H-R66K) | $4.21 \pm 2.66 \cdot 10^{-11}$ | 66 ± 1.98 | 1.4 |
| λ-graft | $3.80 \pm 0.76 \cdot 10^{-10}$ | 16 ± 0.50 | 2.0 |
| κ-graft | $1.57 \pm 0.14 \cdot 10^{-06}$ | 79 ± 2.37 | 2.6 |

The Gal4 AD-scFv Fusion Proteins Perform in a Two Hybrid Assay According to Their in vitro Stability and in vivo Performance.

Figure 3B:
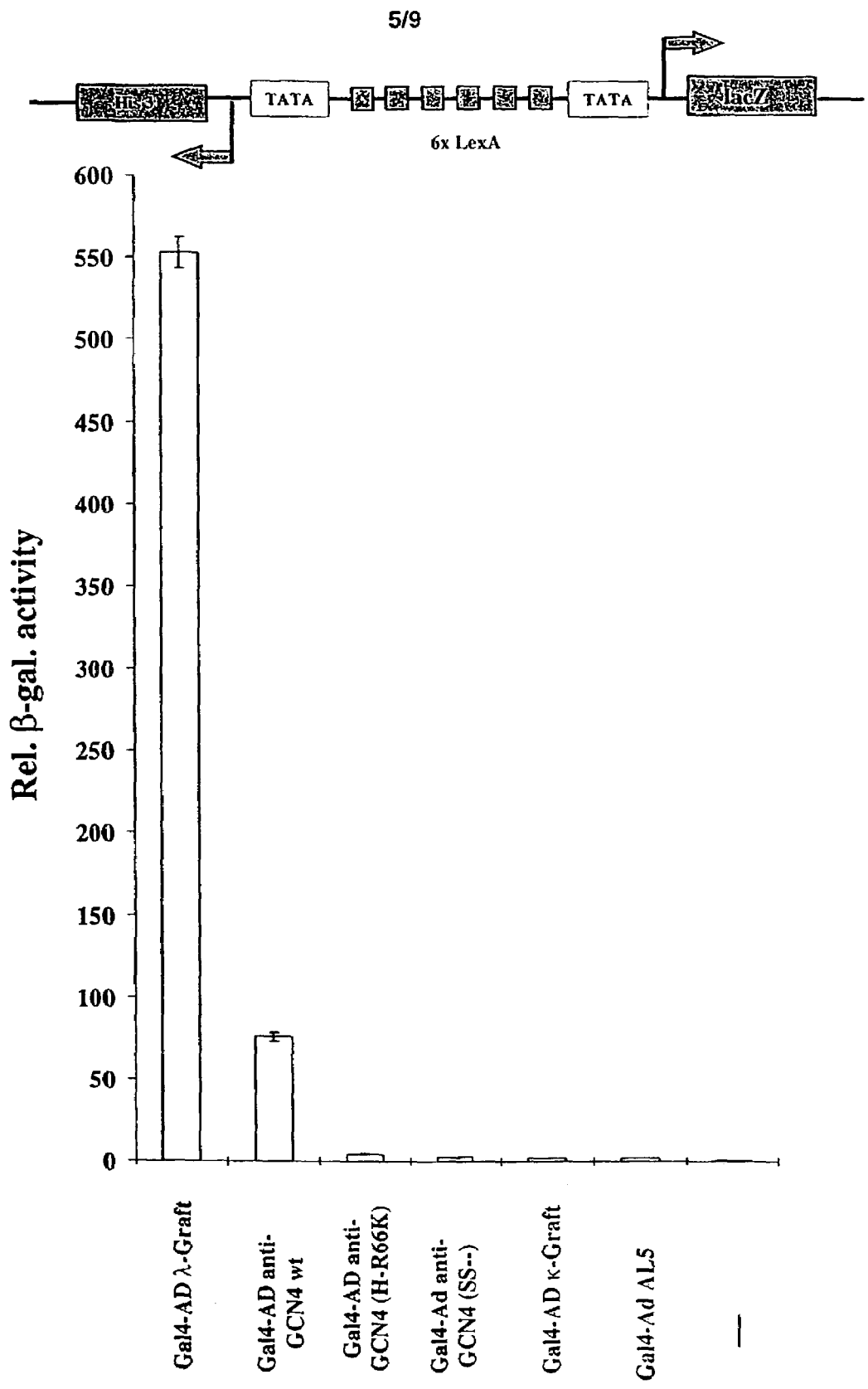
FIG. 3B shows in vivo performance of different scFv fragments expressed in yeast, in a two hybrid assay.

The successful interaction between the antigen and the complementary determining regions (CDRs) in the two hybrid assay monitoring LacZ expression as a reporter gene is shown in FIG. 3B. The reporter strain YDE173 was used. Strain YDE173 was deposited on Feb. 11, 2000 with the Deutsche Sammlung von Mikroorganismen und Zellkulturen DSZM, Braunschweig Germany, under the Number DSM 13333. YDE173 was derived from yeast strain JPY5 (Matα ura3-52 his3Δ200 leu2Δ1 trp1Δ63 lys2Δ385) having integrated at the genomic his3 locus the reporter plasmid pDE200 which contains six LexA binding sites controlling the divergently oriented reporter genes HIS3 and LacZ.

The same scFv fragments as used for FIG. 3A, but fused to the transcriptional activation domain of Gal4 were coexpressed together with the GCN4 leucine zipper (aa 245-285) fused C-terminal to LexA, serving as a bait for the two hybrid assay. The unspecific AL5 control scFv fusion construct was unable to interact with the LexA-GCN4 leucin zipper and therefore did not activate the LacZ reporter gene. The Gal4 activation domain fused to the framework stabilized λ-graft variant exhibited the strongest effect as activating intrabody, followed by the anti-GCN4 wild-type, and the destabilized point mutant anti-GCN4 (H-R66K). In contrast the highly stable but weakly binding κ-graft and the cysteine-free anti-GCN4 (SS⁻⁻) caused no significant reporter gene expression in the two hybrid format. The same results were obtained in an X-Gal plate assay (data not shown). In summary, the in vivo performance of the different Gal4 AD-scFv fusion variants in activating the LacZ reporter gene in the two hybrid format correlates reciprocally to the inhibition pattern of the Gcn4p dependend LacZ expression (compare FIG. 3A with 3B).

Interaction Between the Antigen and the Different scFv's Fused to a Transcriptional Activation Domain Allows Growth Selection in a Two Hybrid Assay Since the integrated reporter construct contains not only a LacZ reporter gene but also the HIS3 gene, it is suitable for growth selection on plates lacking any histidine. Furthermore, by adding different concentration of 3-aminotriazol (3-AT), which is a competitive inhibitor of the HIS3 gene product, it is possible to inhibit (suppress) growth of the yeast cells dependent on the strength of the interaction between bait/antigen and Gal4 AD-scFv.

The experimental procedure leading to the results shown in FIG. 4 was as follows: A serial 5-fold dilution, starting with approximately 10'000 yeast cells coexpressing the GCN4 leucine zipper (aa 245-285) fused to LexA and a Gal4-AD scFv fusion protein, were spotted on drop out plates (-Trp/-Leu/-His) containing different concentrations of 3-AT. Growth was monitored after 48 h, 72 h, and 120 h.

Figure 4:
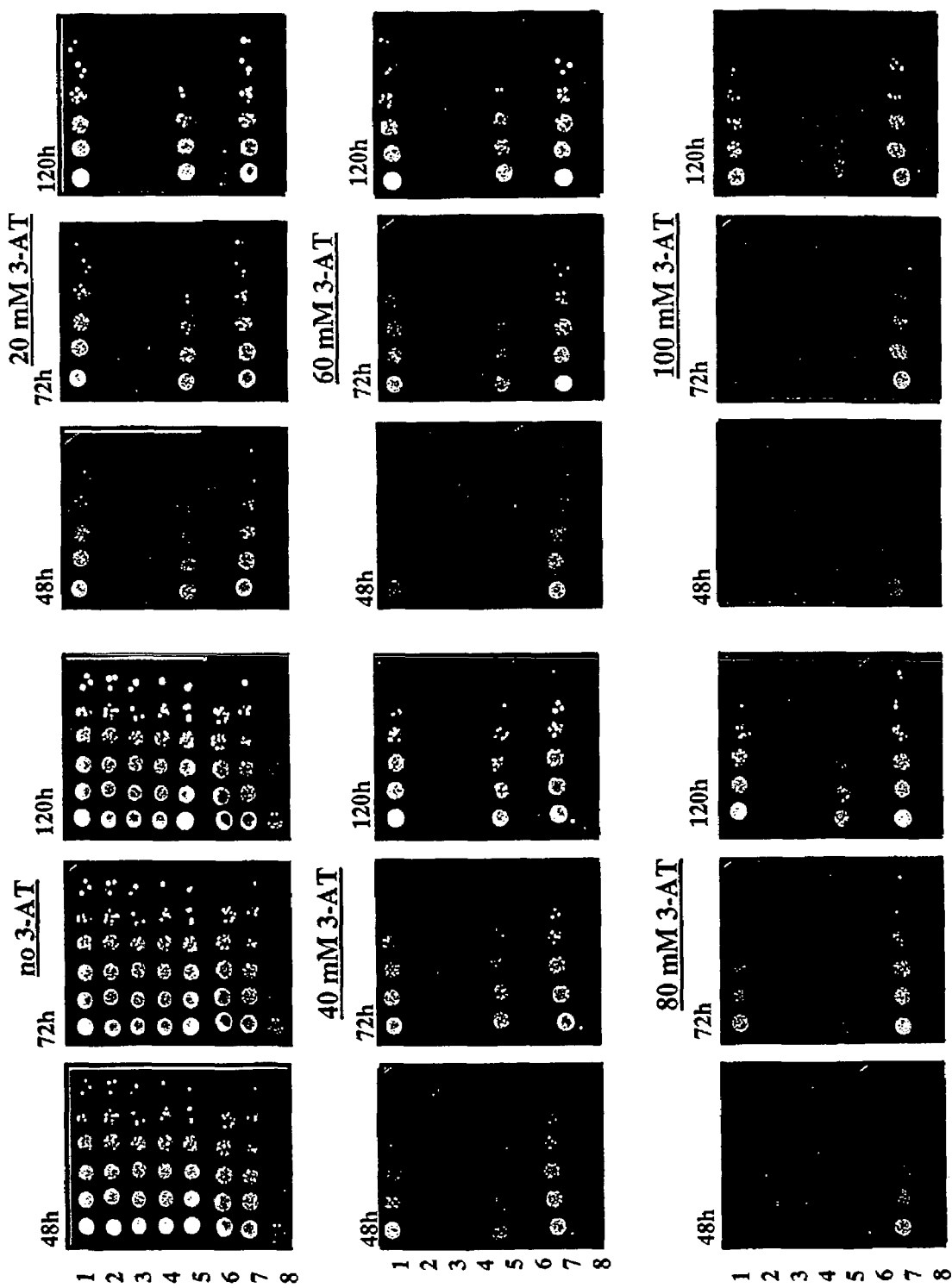
FIG. 4 shows growth selection in a two hybrid assay of cells expressing different scFv fragments.

The lanes in FIG. 4 are as follows:

1. Gal4-AD λ-graft, 2. Gal4-AD AL5, 3. Gal4-AD κ-graft, 4. Gal4-AD anti-GCN4 (SS⁻⁻), 5. Gal4-AD anti-GCN4 wild-type, 6. Gal4-AD Anti-GCN4 (H-R66K), 7. LexA-Gal 11 fusion protein serves as positive control, 8. empty vectors.

Growth of the yeast strains coexpressing the bait/antigen (lexA-GCN4 leucine zipper) together with a Gal4 AD-scFv fusions was monitored over five days. As a control on plates lacking 3-AT, no obvious growth difference of the different Gal4 AD-scFv fusion variants was observed. Already 20 mM 3-AT were enough to suppress growth of the cells transformed with the negative control scFv (Gal4 AD-AL5). In correlation with the results monitoring β-galactosidase expression, the Gal4 AD fusions with the κ-graft variant, anti-GCN4 (SS⁻⁻), and anti-GCN4 (H-R66K) did not allow growth in the presence of 20 mM 3-AT. Cells expressing the λ-graft variant as well as the anti-GCN4 wild-type were able to grow in the presence of up to 80 mM 3-AT within 5 days with a clear advantage for the framework stabilized λ-graft over the time. A concentration of 100 mM 3-AT was enough to abolish growth of cells expressing Gal4 AD-anti-GCN4 wild-type. Only after five days, a few appeared on the most concentrated spotting whereas cells expressing the λ-graft Gal4 AD-scFv fusion variant clearly grew.

Figure 5A:
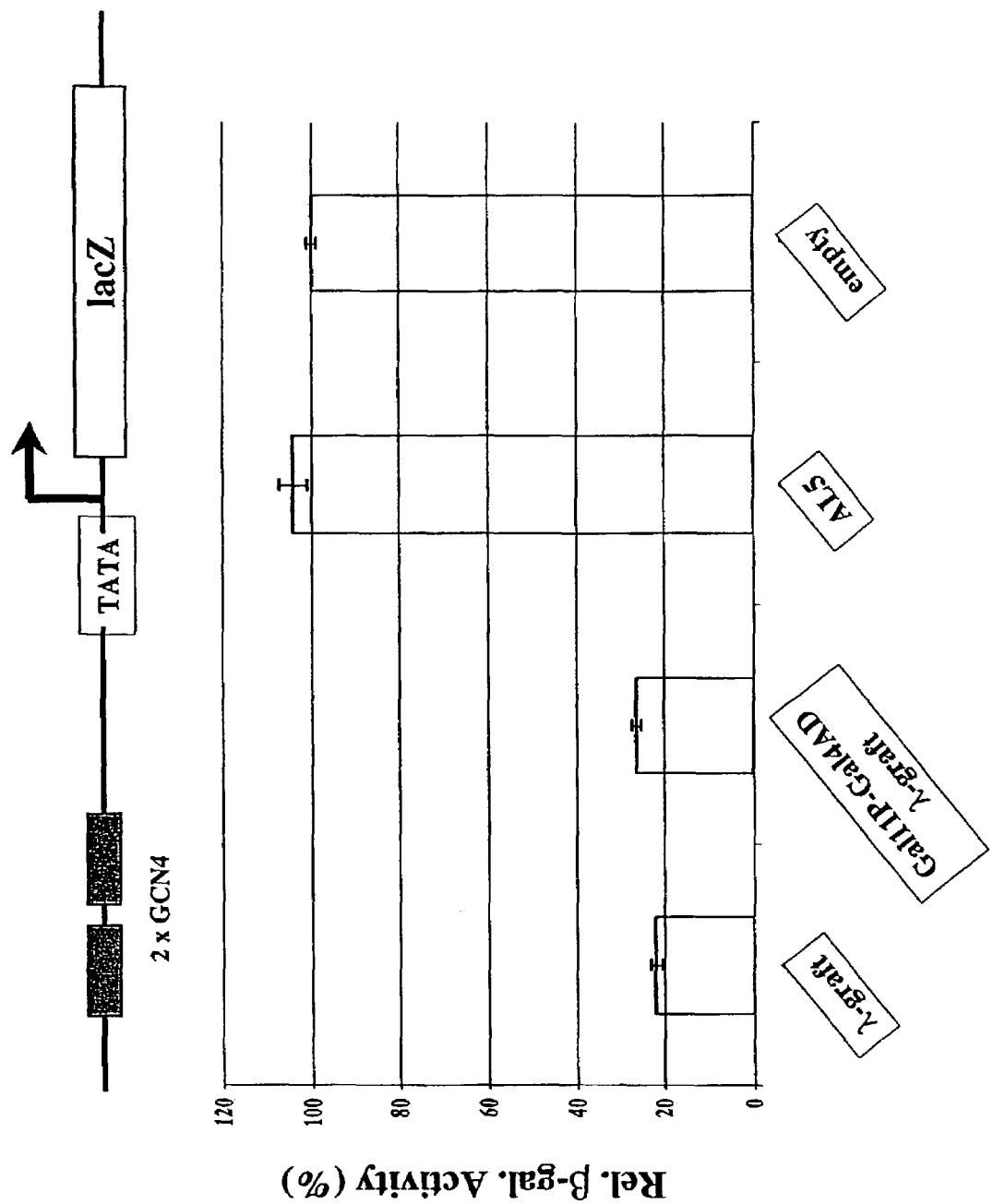
FIG. 5A shows that the N-terminal fusion of a constant domain (Gal11P-Gal4AD) to a single chain antibody does not significantly change the property of this scFv fragment on gene expression of a Gcn4p dependent LacZ reporter

The N-Terminal Fusion of Constant Domain(s) to the λ-Graft scFv does not Interfere with its Biological Activity Gal11P (residues 263-352) and the Gal4 activation domain was fused to the N-terminus of the λ-graft scFv (Gal11P-Gal4AD λ-graft). Its biological activity in inhibiting the Gcn4p dependent gene activation was compared to λ-graft alone. As shown in FIG. 5A the fusion of a constant domain to the scFv did not interfere with the inhibitory activity on Gcn4p dependent gene activation.

Introduction of Specific Restriction Sites

Figure 5B:
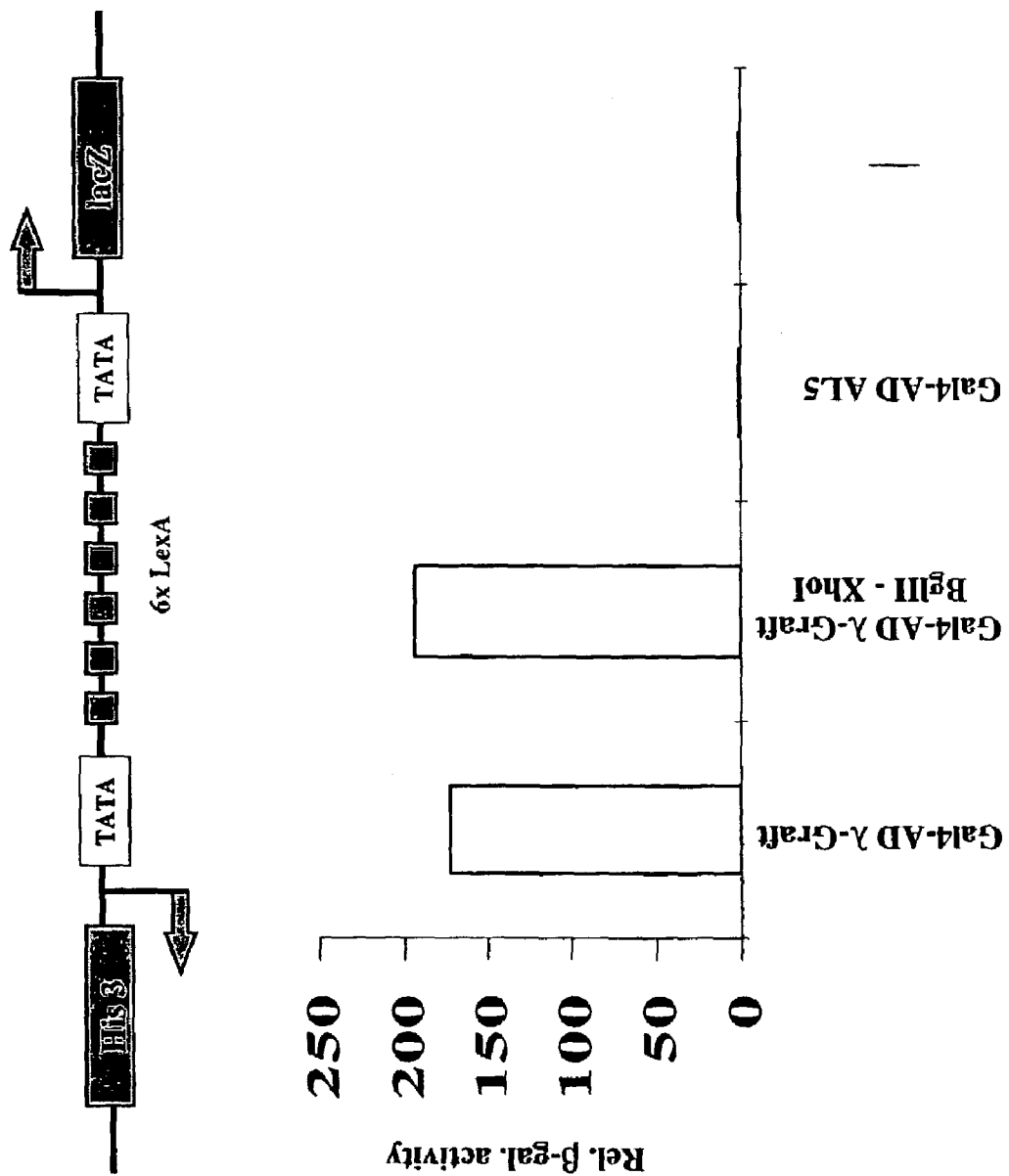
FIG. 5B shows that the introduction of two unique restriction site in a single chain antibody does not change the property of this scFv fragment on gene expression of a LacZ reporter.

In order to exchange the CDR3$V_H$ (GLFDY) (SEQ ID NO: 8) with a random peptide library, two unique restriction sites (BglII and XhoI) flanking this hypervariable region were introduced by silent mutagenesis. These silent changes did not affect the amino acid sequence of the antibody and therefore did not alter the in vivo performance of the λ-graft variant (see FIG. 5B).

The importance of the CDR3 hypervariable region (de Wild et al., 1997; Hemminki et al., 1998) for specific recognition of its antigen (GCN4 leucine zipper) was shown by introducing an additional alanine N-terminal to the CDR3 (AGLFDY) (SEQ ID NO: 9) of the variable heavy chain. This λ-graft+Ala variant failed to inhibit expression of a Gcn4p dependent reporter gene in the yeast strain YAdM 2xGCN4-150, and was also unable to activate reporter gene expression in the two hybrid format using the strain YDE173 (data not shown).

Both Graft Variants are Soluble in Yeast Cytoplasm

Figure 6:
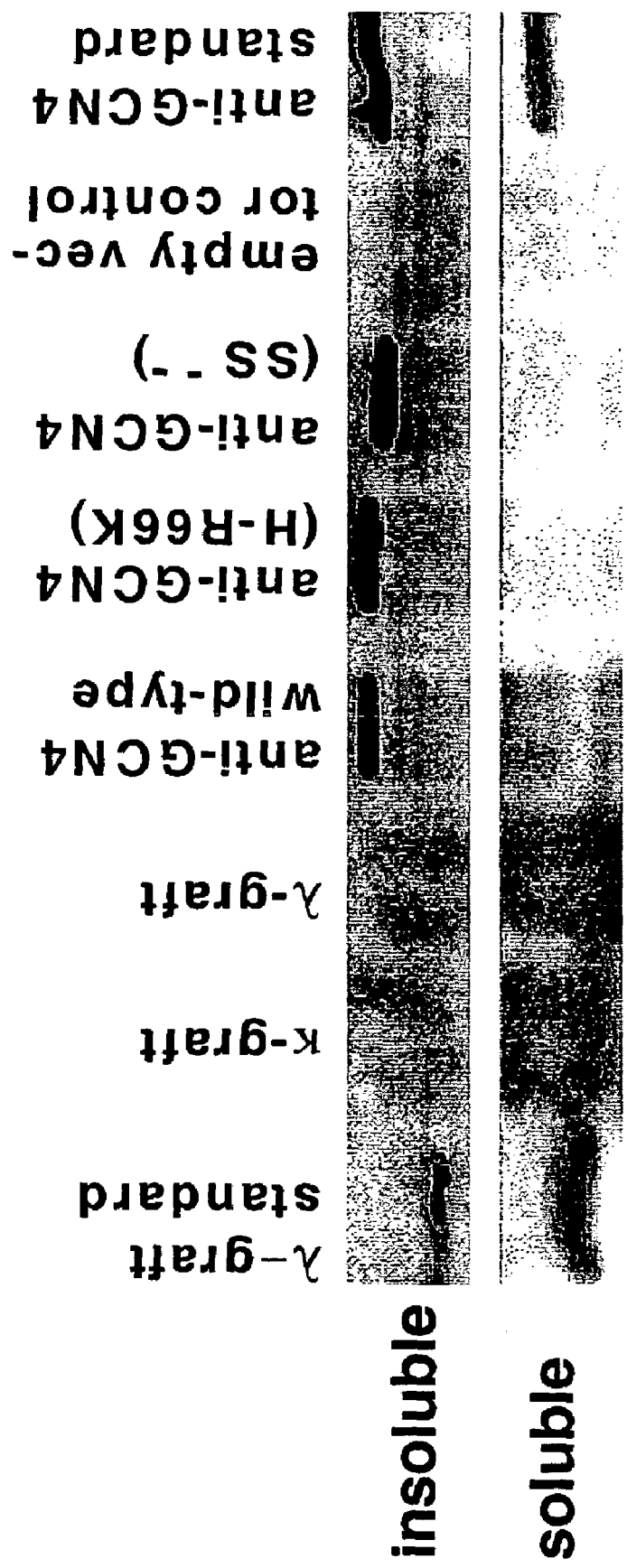
FIG. 6 shows western blot analysis of solubility of different Gcn4p binding scFv fragments expressed in yeast.

The solubility of the different Gcn4p binding scFv fragments in yeast was tested by Western blot analysis. Only in case of the λ- and κ-graft variants significant amounts of soluble protein could be detected in crude cell extracts (FIG. 6).

All other anti-GCN4 scFv fragments appeared to be essentially completely insoluble, with the amount of insoluble scFv slightly increasing with decreasing in vitro stability. However, one has to caution that the exact ratio of soluble to insoluble protein for the different scFv variants may not necessarily reflect the ratio present in vivo. It cannot be excluded that part of the different anti-GCN4 variants might have precipitated during sample preparation, even though we used a gentle cell disruption method, by using the Y-PER™ Yeast Protein Extraction Reagent form Pierce.

Improvement of the Framework

Variations in frameworks preferably isolated by a method according to the present invention can be combined to generate further frameworks that are stable and soluble in a reducing environment. Said resulting frameworks show an enhanced in vivo performance compared to frameworks bearing only one variation. A framework combining six variations is defined in SEQ ID NO:1.

EXAMPLES

Design of CDR-Grafted Anti-GCN4 scFv Fragments
Cloning, Expression and Purification of scFv Fragments
All scFv fragments were in a $V_L$-$V_H$ orientation with a 20-mer linker (GGGGSGGGGSGGGGSSGGGS) (SEQ ID NO: 10) and a D-terminal his$_5$-tag.

The scFv fragments expressed in yeast were cloned into the pESBA-Act expression vector. The pESBA-Act vector is a *Saccharomyces cerevisiae-E.coli* shuttle vector. It contains a bacterial origin of replication and the amp resistance gene. Furthermore it contains the yeast TRP1 gene for transformation selection in *S. cerevisiae*. It is designed for high protein expression in yeast and therefore has the 2 μ origin of replication ensuring high copy numbers in *S. cerevisiae*. In addition, it contains the strong constitutive actin promoter and the GAL11 transcriptional termination sequence separated by a multiple cloning site containing restriction sites for NcoI (covering translational initiation codon ATG), ApaI, StuI, three translational stop codons in all three frames and a SalI site.

All scFv fragments were cloned via Bsp120I and StuI restriction sites and carried a C-terminal His$_5$-tag. Two amino acids (Gly-Pro) encoding the Bsp120I site had to be included at the N-terminus, after the initiating Met residue.

Fusion of the Gal4 AD N-terminal to the various antibody variants.

The Gal4 activation domain was amplified by polymerase chain reaction using pGAD424 (Clontech) as template. Both primers [upstream primer: 5'-CCATGGGC-CCAAGCTTTGCAAAGATGGATAAAG-3' (Seq. Id. No. 2, downstream primer: 5'-TTTGGGCCCGAAGAACCGC-CACCACCAGAACCG CCTCCACCAGAGCCACCAC-CACCAGGCCTGATCTCTTTTTTTGGGTTTGGTG-3', (Seq. Id. No. 3)] contain an ApaI site suitable for cloning the Gal4 activation domain (AD) polypeptide including the SV40 T-antigen nuclear localisation signal N-terminal to the different scFv's in the context of pESBA Act. The activation domain and the single chain antibodies are seperated by a (GGGS)$_3$ linker encoded by the downstream primer.

N-Terminal Fusion of Gal11wt and Gal11P to the Gal4 Activation Domain (AD)-scFv Fusion Gal11wt and Gal11p were both amplified using the following primers: upstream primer: 5'-CATGCCATGGTTC-CTCAACAGCAGCAAATGCAAC-3' (Seq. Id. No. 4), downstream primer: 5'-CATGCCATGGCGCTAGC-CAAAGCTTGGATTTTT CTCAGG-3' (Seq. Id. No. 5), both containing an NcoI site. The PCR products encoding amino acids 263-352 were inserted into the NcoI site of the pESBA-Act2 Gal4(AD)-scFv fusion construct (described above). This generated an in frame fusion of the respective Gal11 allele with Gal4(AD)-scFv. Correct orientation of the Gal11 inserts was checked by digestion with the unique enzyme NheI.

LexA Fusion

The GCN4 leucine zipper (aa 245-285) was PCR amplified with primers containing an EcoRI site convenient for cloning downstream of LexA aa 1-202. This results in pAdM018, an Ars Cen plasmid with the LEU2 selection marker expressing the fusion protein under the control of the ADH promoter.

Introduction of a BglII and XhoI Site Flanking CDR3 of $V_H$

In order to easily exchange the CDR3 of the variable heavy chain, two unique restriction sites were introduced flanking the CDR3 $V_H$ by site directed mutagenesis, without changing the primary structure of the Gal4 AD-λ-graft scFv. These silent point mutations were introduced by PCR using λ-graft as template. In a first round, two seperate PCR reactions were performed using primer #2421 with #2487 and #2486 with #2488 leading to two overlapping PCR products. These two products served as template for the second round of PCR with the outer primer #2421 and #2488 containing a SpeI and SalI site. The final product was subcloned into Gal4 AD-λ-graft using SpeI and SalI.

Direct Intracellular Screening for Novel CDRs Interacting with the Antigen.

The first three amino acids (GLF) of the CDR3 from the variable heavy chain of the framework stabilized λ-graft scFv fused to the Gal4 activation domain (λ-graft scFv-Gal4 AD) were randomized with a PCR based method described by Reiter et al. The last two residues (D and Y) of the CDR3 were not randomized due to their conservation and structural importance (Chothia and Lesk, 1987). A λ-graft scFv-Gal4 AD library potentially encoding 8000 different CDR3 variants of the variable heavy chain was obtained. Sequence analysis of six randomly picked library clones revealed the presence of random CDR3 sequences at the expected positions.

The yeast strain YDE173, containing the HIS3 and LacZ reporter genes under the control of 6 LexA binding sites (see above), was cotransformed with the vector expressing the GCN4 leucine zipper (aa 245-285) fused to LexA and the library and plated on selective drop out plates (-Trp/-Leu/-His) containing 60 mM 3-AT for growth selection. If a scFv fragment from the CDR3 library with a suitable CDR3 sequence binds to the leucine zipper antigen fused to LexA, a complex is formed that activates transcription of the HIS3 reporter gene and restores histidine independent growth of the yeast cell. After 3 days, growing colonies were picked and replated on the same selective drop out plates. Cells that still grew after the second selection were analyzed for β-galactosidase activity on X-gal plates. Library plasmid DNA from β-gal positive clones was extracted and the region of the CDR3 of the variable heavy chain was sequenced: We found four times the original λ-graft CDR3 amino acid sequence and 3 completely new CDR3 sequences specific for the GCN4 leucine zipper. The four identified scFv clones containing the original CDR3 sequence behaved indistinguishable as the λ-graft whereas the three clones with the altered CDR3 sequence were less efficient in activating the LacZ reporter gene.

These results demonstrate the feasibility of a direct intracellular screening for novel CDRs embedded in a defined scFv framework that is stable and soluble under reducing conditions.

Figure 2:
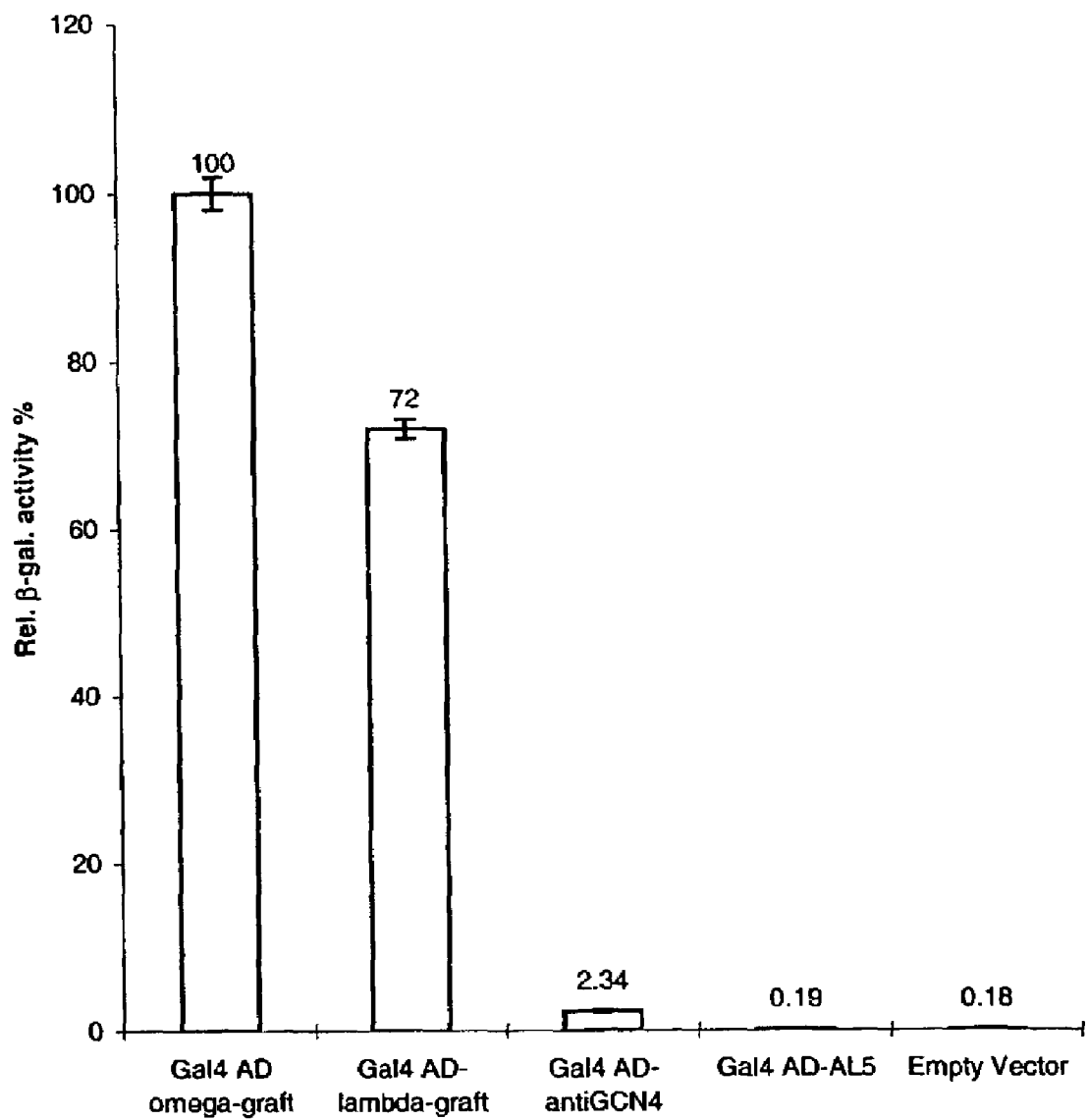
FIG. 2 shows the better in vivo performance of the optimized Gal4 AD-Ω-graft scFv compared to another variant called λ-graft.

In vivo Performance of a Defined Intrabody can be Optimized by Random Mutagenesis The framework stabilized λ-graft variant was randomly mutagenized by PCR as described by Sambrook et al. in order to statistically introduce amino acid changes along the framework of the intrabody. The yeast strain YDE173 was cotransformed with this random mutagenized scFv library fused to the activation domain of Gal4 and the plasmid expressing the specific antigen (aa 245-258 of the GCN4 leucine zipper) fused to LexA and grown on drop out plates containing 80 mM 3-AT. Six candidate clones were selected, each bearing one single amino acid change in the framework. All these six mutant frameworks showed an improved in vivo performance compared to the λ-graft variant, which was confirmed and quantitated by measuring the β-galactosidase activity. With the assumption that different amino acid changes which improve the performance of an intrabody behave additively, we combined all six mutations in one framework which was fused to the Gal4 activation domain and compared it with the framework stabilized λ-graft variant in activating the LacZ reporter gene. FIG. 2 shows that this new framework which has all six point mutations combined (Ω-graft) displays an almost 30% better in vivo performance compared to the original λ-graft variant. Remarkably, these six amino acid substitutions are clustered; two of them (E→K and L→R are preceding the CDR1 of the variable light chain and the remaining four (N→D, G→C, K→E, T→S) are located between CDR2 and CDR3 of the variable heavy chain.

Integration of a Reporter Gene into the Chromosome of *Saccharomyces cerevisiae*

The integrating reporter plasmid pAB183 was derived from pJP161 (Barberis et al., 1995) by cloning two Gcn4p binding sites at position 150 upstream of the TATA box of the GAL1 promoter. The Gcn4p binding sites were generated by annealing two complementary oligonucleotides having a 5' SphI and 3' SalI compatible overhang sequence. The oligonucleotides are as follows: 5'-CCTATGACTCATC-CAGTTATGACTCATCG-3' (Seq. Id. No. 7). This reporter plasmid was linearized at the ApaI site and integrated into the yeast genomic ura3 locus of strain JPY5 (Barberis et al., 1995), resulting in YAdM2xGCN4-150. Strain YAdM2xGCN4-150 was deposited on Feb. 11, 2000 with the Deutsche Sammlung von Mikroorganismen und Zellkulturen GmbH DSZM, Braunschweig Germany, with the Number DSM13332. Four independent yeast transformants were tested in a functional assay and all showed the same GCN4-dependent reporter gene activity. One of the clones (YAdM2xGCN4-150) was chosen for all subsequent experiments and is called yeast wild-type.

The reporter strain used for the two hybrid experiments, has a integrated reporter construct containing a bidirectional promoter with six LexA binding sites driving LacZ and HIS3 expression.

Serial Dilution and Spotting of Yeast Cells

Yeast cells were transformed using the lithium acetate method, following standard protocols. Transformants were grown over night at 30° C. in drop-out medium (-Trp/-Leu). The saturated cultures were diluted in dropout medium to $OD_{600}=0.7$ and incubated again for at least one duplication time. Each culture was serially diluted in water (dilution factor 5) starting with an approximate concentration of $10^6$ cells/ml, and 10 µl of each dilution were spotted on drop-out plates (-Trp/-Leu/-His) containing 0 mM, 20 mM, 40 mm, 60 mM, 80 mM, or 100 mM of 3-aminotriazole. Six different dilutions of each transformant were spotted on drop-out plates. The plates were incubated at 30° C. and scanned after 48 h, 72 h, and 120 h.

In vivo Analysis of scFv Fragments: Expression of scFv Fragments in Yeast and the β-galactosidase reporter assay The β-galactosidase assay in solution was performed using permeabilized cells as described (Kaiser et al., 1994, Escher and Schaffner 1997). Activity was normalized to the number of cells assayed.

Western Blot Analysis of Anti-GCN4 scFv Fragments

The solubility of the different anti-GCN4 scFv fragments was analyzed by Western blot. Five ml cultures were grown at 30° C. to an optical density of about 2-3. Cells were normalized to same cell densities, pelleted and whole cell protein was extracted with Y-PER™ Yeast Protein Extraction Reagent form Pierce, which is a mild detergent formulation facilitating gentle isolation of soluble proteins. Soluble and insoluble fractions were separated by centrifugation (13000 rpm, 10 min, 4° C.). Samples of soluble and insoluble crude extract were subjected to SDS-PAGE and blotted on PVDF membranes, following standard protocols. Hiss-tagged scFv fragments were detected with anti-Hiss scFv-AP fusion as described (Lindner et al., 1997), with the chemoluminescent phosphatase substrate CSPD from Boehringer Mannheim. To obtain reasonable intensities on the Western blots, about 5 times higher protein concentrations had to be used in the soluble fractions, compared with the insoluble fractions and the blots were exposed for different time spans. Thus, a direct comparison is only meaningful between all soluble or all insoluble samples, respectively.

While there are shown and described presently preferred embodiments of the invention, it is to be distinctly understood that the invention is not limited thereto but may be otherwise variously embodied and practiced within the scope of the following claims.

REFERENCES CITED

Barberis, A., Pearlberg, J., Simkovich, N., Farrell, S., Reinagel, P., Bamdad, C., Sigal, G. and Ptashne, M. (1995) Contact with a component of the polymerase II holoenzyme suffices for gene activation. *Cell*, 81, 359-368.

Beerli, R. R., Wels, W. and Hynes, N. E. (1994) Intracellular expression of single chain antibodies reverts ErbB-2 transformation. *J Biol Chem*, 269, 23931-6.

Berger, C., Weber-Bornhauser, S., Eggenberger, J., Hanes, J., Plückthun, A. and Bosshard, H. R. (1999) Antigen recognition by conformational selection. *FEBS Lett.*, 450, 149-153.

Biocca, S., Pierandrei-Amaldi, P., Campioni, N. and Cattaneo, A. (1994) Intracellular immunization with cytosolic recombinant antibodies. *Bio/Technology*, 12, 396-9.

Biocca, S., Ruberti, F., Tafani, M., Pierandrei-Amaldi, P. and Cattaneo, A. (1995) Redox state of single chain Fv fragments targeted to the endoplasmic reticulum, cytosol and mitochondria. *Bio/Technology*, 13, 1110-5.

Cattaneo, A. (1998) Selection of intracellular antibodies. *Bratisl Lek Listy*, 99, 413-8.

Cattaneo, A. and Biocca, S. (1999) The selection of intracellular antibodies. Trends In Biotechnology, 17, 115-21.

Derman, A. I., Prinz, W. A., Belin, D. and Beckwith, J. (1993) Mutations that allow disulfide bond formation in the cytoplasm of *Escherichia coli*. *Science*, 262, 1744-7.

De Wildt, R M., Ruytenbeek, R., van Venrooij, W J., and Hoet, R M. (1997). Heavy chain CDR3 optimization of a germline encoded recombinant antibody fragment predisposed to bind the U1A protein. *Protein Eng.*, 10, 835-841.

Duan, L., Bagasra, O, Laughlin, M. A., Oakes, J. W. and Pomerantz, R. J. (1994) Potent inhibition of human immunodeficiency virus type 1 replication by an intracellular anti-Rev single-chain antibody. *Proceedings of the National Academy of Sciences of the United States of America*, 91, 5075-9.

Escher, D. and Schaffner, W. (1997) Gene activation at a distance and telomeric silencing are not affected by yeast histone H1. *Mol. Gen. Genet.*, 256, 456-461.

Freund, C., Ross, A., Guth, B., Plückthun, A. and Holak, T. A. (1993) Characterization of the linker peptide of the single-chain Fv fragment of an antibody by NMR spectroscopy. *FEBS Lett.*, 320, 97-100.

Gargano, N. and Cattaneo, A. (1997) Rescue of a neutralizing anti-viral antibody fragment from an intracellular polyclonal repertoire expressed in mammalian cells. *FEBS Lett*, 414, 537-40.

Ge, L., Knappik, A., Pack, P., Freund, C. and Plückthun, A. (1995) Expressing antibodies in *Escherichia coli*. In *Antibody Engineering* (2nd edn). Borrebaeck, C. A. K. (ed.), Oxford University Press, pp 229-266.

Greenman, J., Jones, E., Wright, M. D. and Barclay, A. N. (1996) The use of intracellular single-chain antibody fragments to inhibit specifically the expression of cell surface molecules. *J Immunol Methods*, 194, 169-80.

Hanes, J., Jermutus, L., Weber-Bornhauser, S., Bosshard, H. R. and Plückthun, A. (1998) Ribosome display efficiently selects and evolves high-affinity antibodies in vitro from immune libraries. *Proc. Natl. Acad. Sci. USA*, 95, 14130-14135.

Hemminki, A., Niemi, S., Hoffren, A M., Hakalahti, L., Soderlund, H., and Takkinen, K. (1998). Specific improvement of a recombinant anti-testosterone Fab fragment by CDR3 mutagenesis and phage display selection. *Protein Eng.*, 11, 311-319.

Hoogenboom, H. R., de Bruine, A. P., Hufton, S. E., Hoet, R. M., Arends, J. W. and Roovers, R. C. (1998) Antibody phage display technology and its applications. *Immunotechnology*, 4, 1-20.

Jones, P. T., Dear, P. H., Foote, J., Neuberger, M. S. and Winter, G. (1986) Replacing the complementarity-determining regions in a human antibody with those from a mouse. *Nature*, 321, 522-525.

Kabat, E. A., Wu, T. T., Perry, H. M., Gottesman, K. S. and Foeller, C. (1991) Variable region heavy chain sequences. In Sequences of Proteins of Immunological Interest. *NIH Publication No.* 91-3242, National Technical Information Service (NTIS).

Kaiser, C., Michaelis, S. and Mitchell, A. (1994) Assay of β-galactosidase in yeast. In *Methods in yeast genetics*. Cold Spring Harbour Laboratory Press, New York, pp. 169-173.

Kipriyanov, S. M., Moldenhauer, G., Martin, A. C., Kupriyanova, O. A. and Little, M. (1997) Two amino acid mutations in an anti-human CD3 single chain Fv antibody fragment that affect the yield on bacterial secretion but not the affinity. *Protein Engineering*, 10, 445-53.

Knappik, A., Krebber, C. and Plückthun, A. (1993) The effect of folding catalysts on the in vivo folding process of different antibody fragments expressed in *Escherichi coli*. *Biotechnology*, 11, 77-83.

Knappik, A. and Plückthun, A. (1995) Engineered turns of a recombinant antibody improve its in vivo folding. *Protein Engineering*, 8, 81-9.

Krebber, A., Bornhauser, S., Burmester, J., Honegger, A., Willuda, J., Bosshard, H. R. and Plückthun, A. (1997) Reliable cloning of functional antibody variable domains from hybridomas and spleen cell repertoires employing a reengineered phage display system. *J. Immunol. Meth.*, 201, 35-55.

Kyoko, T., Toshifumi, Y., Toshiro, T. and Tomoyasu, R. (1999) Production of antibody Fab fragment using yeast JP11000174.

Martineau, P., Jones, P. and Winter, G. (1998) Expression of an antibody fragment at high levels in the bacterial cytoplasm. *Journal of Molecular Biology*, 280, 117-27.

Mhashilkar, A. M., Bagley, J., Chen, S. Y., Szilvay, A. M., Helland, D. G. and Marasco, W. A. (1995) Inhibition of HIV-1 Tat-mediated LTR transactivation and HIV-1 infection by anti-Tat single chain intrabodies. *EMBO Journal*, 14, 1542-51.

Leder, L., Berger, C., Bornhauser, S., Wendt, H., Ackermann, F., Jelesarov, I. and Bosshard, H. R. (1995) Spectroscopic, calorimetric, and kinetic demonstration of conformational adaption in peptide-antibody recognition. *Biochemistry*, 34, 16509-16518.

Lindner, P., Bauer, K., Krebber, A., Nieba, L., Kremmer, E., Krebber, C., Honegger, A., Klinger, B., Mocikat, R. and Plückthun, A. (1997) Specific detection of his-tagged proteins with recombinant anti-His tag scFv-phosphatase or scFv-phage fusions. *BioTechniques*, 22, 140-149.

Pace, C. N. (1990) Measuring and increasing protein stability. *Trends Biotech.*, 8, 93-98.

Proba, K., Wörn, A., Honegger, A. and Plückthun, A. (1998) Antibody scFv fragments without disulfide bonds made by molecular evolution. *J. Mol. Biol.*, 275, 245-253.

Reiter, Y., Schuck, P., Boyd, L. F. and Plaksin, D. (1999). An antibody single-domain phage display library of a native heavy chain variable region: Isolation of functional single-domain VH molecules with a unique interface. *J. Mol. Biol.* 290, 685-698.

Sambrook, J., Fritsch, E. F. and Maniatis, T. (1989). Molecular cloning. A laboratory manual, second edition. Cold Spring Harbor Laboratory Press 1989.

Studier, F. W. and Moffatt, B. A. (1986) Use of bacteriophage T7 RNA polymerase to direct selective high-level expression of cloned genes. *J. Mol. Biol.,* 189, 13-130.

Tavladoraki, P., Benvenuto, E., Trinca, S., De Martinis, D., Cattaneo, A. and Galeffi, P. (1993) Transgenic plants expressing a functional single-chain Fv antibody are specifically protected from virus attack. *Nature,* 366, 469-72.

Ulrich, H. D., Patten, P. A., Yang, P. L., Romesberg, F. E. and Schultz, P. G. (1995) Expression studies of catalytic antibodies. *Proceedings of the National academy of Sciences of the United States of America,* 92, 11907-11.

Visintin M., Tse E., Axelson H., Rabbitts .H. and Cattaneo A. (1999) Selection of antibodies for intracellular function using a two-hybrid in vivo system. *Proceedings of the National Academy of Sciences of the United States of America,* 96, 11723-11728.

Wörn, A. and Plückthun, A. (1998a) Mutual stabilization of $V_L$ and $V_H$ in single-chain antibody fragments, investigated with mutants engineered for stability. *Biochemistry,* 37, 13120-13127.

Wörn, A. and Plückthun, A. (1998b) An intrinsically stable antibody scFv fragment can tolerate the loss of both disulfide bonds and fold correctly. *FEBS Lett.,* 237, 357-361.

Wörn, A. and Plückthun, A. (1999) Different equilibrium stability behavior of scFv fragments: Identification, classification and improvement by protein engineering. Biochemistry, 38, 8739-8750.

The invention claimed is:

1. A method for screening for intrabodies with CDRs interacting with a specific antigen comprising:
   (a) identification of intrabody framework which is soluble and stable in a reducing environment by a method which comprises the following steps:
      i) transformation of suitable host cells with a nucleic acid library, said library encoding a fusion protein comprising an intrabody and a transcriptional activation domain wherein said transcriptional activation domain is only active as part of a fusion protein comprising an intrabody moiety which is soluble and stable in a reducing environment, and
      ii) culturing said cells under conditions allowing the identification and selection of cells expressing a fusion protein comprising an intrabody moiety which is soluble and stable in a reducing environment by detection of a reporter gene that is expressed by the interaction of the transcriptional activation domain with a DNA binding domain in the host cell wherein the interaction of the transcriptional activation domain with the DNA binding domain results in the growth or identification of cells indicating that the intrabody frameworks or intrabodies are stable and soluble under reducing conditions and is not dependent upon the presence of the antigen for which the intrabody is specific and identifying intrabody frameworks that are soluble and stable in a reducing environment;
   (b) preparation of a randomized intrabody CDR library by exchanging at least one nucleic acid sequence encoding a CDR in an intrabody with a framework which has been identified by the method of step a);
   (c) transformation of host cells with a randomized intrabody CDR library of step (b) and with a nucleic acid sequence encoding a known antigen, whereby the antigen and/or the intrabody of the CDR library are linked to a marker system or part of a marker system such that the cells cultured under selective conditions only survive in the presence of antigen/intrabody-interaction which activates the marker system;
   (d) cultivation of the cells under selective conditions allowing cell survival only in the presence of antigen/intrabody-interaction; and
   (e) harvesting the intrabodies interacting with the known antigen from surviving cells.

2. The method of claim 1, wherein said marker protein of step a) has a selectable activity, which is an enzymatic activity or a fluorescence activity.

3. The method of claim 1, wherein the cell is an eukaryotic cell.

4. The method of claim 1 wherein the DNA sequence encoding the antigen and the DNA sequence encoding the scFv both encode chimeric molecules with the antigen or scFv, respectively, both linked to part of a transcription activating system linked to a survival allowing marker.

5. The method of claim 4, wherein the antigen is fused to a DNA binding domain and the scFv is fused to a transcriptional activator domain or the antigen is fused to a transcriptional activator domain and the scFv is fused to a DNA binding domain.

6. The method of claim 3 wherein the cell is a yeast cell.

* * * * *

SEQUENCE LISTING

```
<160> NUMBER OF SEQ ID NOS: 7

<210> SEQ ID NO 1
<211> LENGTH: 252
<212> TYPE: PRT
<213> ORGANISM: Artificial Sequence
<220> FEATURE:
<221> NAME/KEY: CHAIN
<222> LOCATION: (1)..(114)
<223> OTHER INFORMATION: Variable light chain
<220> FEATURE:
<221> NAME/KEY: CHAIN
<222> LOCATION: (135)..(247)
<223> OTHER INFORMATION: Variable heavy chain
<220> FEATURE:
<221> NAME/KEY: REPEAT
<222> LOCATION: (115)..(134)
<223> OTHER INFORMATION: Glycine Serine Linker
<220> FEATURE:
<221> NAME/KEY: PEPTIDE
<222> LOCATION: (248)..(252)
<223> OTHER INFORMATION: His Tag
<220> FEATURE:
<221> NAME/KEY: DOMAIN
<222> LOCATION: (27)..(39)
<223> OTHER INFORMATION: CDR 1 VL
<220> FEATURE:
<221> NAME/KEY: DOMAIN
<222> LOCATION: (56)..(62)
<223> OTHER INFORMATION: CDR 2 VL
<220> FEATURE:
<221> NAME/KEY: DOMAIN
<222> LOCATION: (95)..(103)
<223> OTHER INFORMATION: CDR 3 VL
<220> FEATURE:
<221> NAME/KEY: DOMAIN
<222> LOCATION: (165)..(169)
<223> OTHER INFORMATION: CDR 1 VH
<220> FEATURE:
<221> NAME/KEY: DOMAIN
<222> LOCATION: (184)..(198)
<223> OTHER INFORMATION: CDR 2 VH
<220> FEATURE:
<221> NAME/KEY: DOMAIN
<222> LOCATION: (232)..(236)
<223> OTHER INFORMATION: CDR 3 VH
<220> FEATURE:
<223> OTHER INFORMATION: Description of Artificial Sequence: Intrabody
      framework

<400> SEQUENCE: 1

Met Gly Pro Asp Ile Val Met Thr Gln Ser Pro Ser Ser Leu Ser Ala
 1               5                   10                  15
```

Ser Val Gly Asp Arg Val Thr Ile Thr Cys Arg Ser Ser Thr Gly Ala
            20                  25                  30

Val Thr Thr Ser Asn Tyr Ala Ser Trp Val Gln Lys Lys Pro Gly Lys
        35                  40                  45

Arg Phe Lys Gly Leu Ile Gly Gly Thr Asn Asn Arg Ala Pro Gly Val
    50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
            100                 105                 110

Lys Arg Gly Gly Gly Gly Ser Gly Gly Gly Ser Gly Gly Gly Gly
        115                 120                 125

Ser Ser Gly Gly Gly Ser Glu Val Lys Leu Leu Glu Ser Gly Gly Gly
    130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
            180                 185                 190

Tyr Asn Ser Ala Leu Lys Asp Arg Phe Ile Ile Ser Lys Asp Asp Cys
        195                 200                 205

Glu Asn Ser Val Tyr Leu Gln Met Ser Lys Val Arg Ser Asp Asp Thr
    210                 215                 220

Ala Leu Tyr Tyr Cys Val Thr Gly Leu Phe Asp Tyr Trp Gly Gln Gly
225                 230                 235                 240

Thr Leu Val Thr Val Ser Ser His His His His His
                245                 250

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 2
ccatgggccc aagctttgca aagatggata aag                                33

<210> SEQ ID NO 3
<211> LENGTH: 83
<212> TYPE: DNA
<213> ORGANISM: Artificial Sequence
<220> FEATURE:
<223> OTHER INFORMATION: Description of Artificial Sequence: PCR Primer

<400> SEQUENCE: 3
tttgggcccg aagaaccgcc accagaaccg cctccaccag agccaccacc accaaggcct      60
gatctctttt tttgggtttg gtg                                             83

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: PCR Primer -continued

```
<400> SEQUENCE: 4
catgccatgg ttcctcaaca gcagcaaatg caac                                  34

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: PCR Primer

<400> SEQUENCE: 5
catgccatgg cgctagccaa agcttggatt tttctcagg                             39

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 6
cctatgactc atccagttat gactcatcg                                        29

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: PCR Primer

<400> SEQUENCE: 7
tcgacgatga gtcataactg gatgagtcat aggcatg                               37
```